United States Patent
Ikeno et al.

(10) Patent No.: US 6,465,668 B2
(45) Date of Patent: Oct. 15, 2002

(54) METHOD FOR PRODUCING FLUOROARYL METAL COMPOUND

(75) Inventors: Ikuyo Ikeno, Osaka; Hitoshi Mitsui, Kitakatsuragi-gun; Toshiya Iida, Suita; Toshimitsu Moriguchi, Takatsuki, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/993,892

(22) Filed: Nov. 27, 2001

(65) Prior Publication Data

US 2002/0065426 A1 May 30, 2002

(30) Foreign Application Priority Data

Nov. 29, 2000 (JP) ........................................ 2000-367746

(51) Int. Cl.$^7$ .............................. C07F 7/22; C07F 7/30; C07F 7/02
(52) U.S. Cl. ......................................... 556/96; 556/480
(58) Field of Search ..................................... 556/96, 480

(56) References Cited

U.S. PATENT DOCUMENTS 3,392,178 A * 7/1968 Tamborski ............... 252/400.1
6,235,222 B1 5/2001 Mitsui et al. ........... 260/665 G

FOREIGN PATENT DOCUMENTS

WO    WO 00/17208    3/2000

OTHER PUBLICATIONS

"Polyfluoroaryl Organometallic Compounds. Part 1. Pentafluorophenyl Derivatives of Tin"; by R.D. Chambers et al.; *Journal of American Chemical Society*; Jan. 24, 1964; pp 4782–4790.

"Synthesis, Properties, and Hydroboration Activity of the Highly Electrophilic Borane Bis (pentafluorophenyl)borane, $HB(C_6F_5)2^{1}$"; by Daniel J. Parks et al.; *Organometallics*, Aug. 5, 1998, pp 5492–5503.

* cited by examiner

*Primary Examiner*—Porfirio Nazario-Gonzalez
(74) *Attorney, Agent, or Firm*—Nixon & Vanderhye P.C.; Frank P. Presta

(57) ABSTRACT

A method for easily and inexpensively producing and purifying a fluoroaryl metal compound such as bis(pentafluorophenyl)dialkyltin which is less colored and has no impurities is provided. Hydrocarbon magnesium halide is reacted with fluoroaryl halide in a solvent including an ether solvent so as to obtain fluoroaryl magnesium halide, which is then reacted with an organic metal compound so as to produce a fluoroaryl metal compound. Tin is more preferable as a metal atom included in the organic metal compound. As for the ether solvent, chain ether solvents are preferable, more specifically, diisopropyl ether, dibutyl ether, and t-butylmethyl ether are more preferable. Besides, it is preferable that magnesium halide, which is a by-product of the fluoroaryl metal compound, is precipitated and removed, or treated with an acid.

13 Claims, No Drawings

METHOD FOR PRODUCING FLUOROARYL METAL COMPOUND

FIELD OF THE INVENTION

The present invention relates to a method for producing a fluoroaryl metal compound such as bis(pentafluorophenyl) dimethyltin or bis(pentafluorophenyl)dibutyltin, which is useful, for example, as a pharmaceutical and agricultural chemical intermediate, a polymerization catalyst, a polymerization co-catalyst, a catalyst for photopolymerization of silicone, and intermediates of these catalysts.

BACKGROUND OF THE INVENTION

A fluoroaryl metal compound such as bis (pentafluorophenyl)dimethyltin or bis(pentafluorophenyl) dibutyltin is a useful compound, for example, as a pharmaceutical and agricultural chemical intermediate, a polymerization catalyst, a polymerization co-catalyst, a catalyst for photopolymerization of silicone, and intermediates of these catalysts.

For example, J. Chem. Soc., (1964) 4782 discloses a method for reacting pentafluorophenyl magnesium bromide (a Grignard reagent), obtained by reacting bromopentafluorobenzene with magnesium using diethyl ether as a solvent, with dimethyltin dibromide over two days at a reflux temperature, and for synthesizing bis(pentafluorophenyl) dimethyltin in a yield of 58 percent.

Besides, for example, Japanese Unexamined Patent Publication No. 2000-191666 (Tokukai 2000-191666, published on Jul. 11, 2000: corresponding U.S. Pat. No. 6,235,222) discloses a method for safely, efficiently, and industrially producing fluoroaryl magnesium halide having no impurities such as a coloring ingredient, through a reaction milder than a conventional method, by performing the Grignard exchange reaction of hydrocarbon magnesium halide such as magnesium methyl bromide and fluoroaryl halide such as bromopentafluorobenzene in a solvent including a chain ether solvent.

Further, for example, Organometallics., (1998) 5492 discloses a method for reacting pentafluorophenyllithium, obtained by reacting bromopentafluorobenzene with butyllithium at −78° C. using diethyl ether as a solvent, with dimethyltin dichloride at −78° C., and for synthesizing bis(pentafluorophenyl)dimethyltin in a yield of 95 percent.

However, in the production method described in J. Chem. Soc., (1964) 4782, since diethyl ether, which is a compound having a low boiling point, is used as the solvent, it is difficult to control the temperature of a reaction system, and special caution is required in handling diethyl ether as it is highly flammable. In addition, a diethyl ether solution of pentafluorophenyl magnesium bromide, obtained by reacting bromopentafluorobenzene with magnesium, is colored in black by impurities formed by a side reaction, etc. Therefore, the bis (pentafluorophenyl) dimethyltin obtained by reacting pentafluorophenyl magnesium bromide with dimethyltin dibromide is colored in black, and in order to purify the bis(pentafluorophenyl)dimethyltin, it is necessary to distill the reaction solution which contains the compound.

Further, in the foregoing production method, the reaction of pentafluorophenyl magnesium bromide and dimethyltin dibromide produces not only the bis(pentafluorophenyl) dimethyltin, which is an object, but also magnesium dibromide, which is magnesium halide, as a by-product. Since magnesium dibromide is soluble in a solvent such as diethyl ether, in order to purify the bis(pentafluorophenyl) dimethyltin, it is necessary to remove the magnesium dibromide from a solution. Besides, J. Chem. Soc., (1964) 4782 discloses a method for removing magnesium halide by treating a reaction solution containing the magnesium halide using an aqueous ammonium chloride solution. However, when the reaction solution is treated with the aqueous ammonium chloride solution, it becomes difficult to separate an organic layer and an aqueous layer. Therefore, it is hard to say that the production method described in J. Chem. Soc., (1964) 4782 is industrially advantageous. Incidentally, when a fluoroaryl metal compound which includes magnesium halide as an impurity is used, for example, as a polymerization catalyst, the activity of the catalyst is significantly decreased.

The problem that pentafluorophenyl magnesium bromide is colored by impurities formed by a side reaction, etc. described in J. Chem. Soc., (1964) 4782 can be solved by obtaining pentafluorophenyl magnesium halide having no impurities such as a coloring ingredient by the Grignard exchange reaction in the method for producing fluoroaryl magnesium halide disclosed in Japanese Unexamined Patent Publication No. 2000-191666 (Tokukai 2000-191666, published on Jul. 11, 2000: corresponding U.S. Pat. No. 6,235,222). However, Japanese Unexamined Patent Publication No. 2000-191666 does not have descriptions that tin is further reacted with fluoroaryl magnesium halide, and that fluoroaryl magnesium halide can be used as a raw material, as an intermediate of a specific fluoroaryl metal compound, etc.

On the other hand, in the production method described in Organometallics., (1998) 5492, the reaction system should be cooled down to −78° C., which is difficult to carry out industrially.

Consequently, a method for producing and purifying a fluoroaryl metal compound easily and inexpensively has been desired.

SUMMARY OF THE INVENTION

It is therefore an object of the present invention to provide a method for producing and purifying a fluoroaryl metal compound which has no impurities and is less colored, easily and inexpensively.

To solve the foregoing problems, in the present invention, consideration has been given to various synthesis routes other than the foregoing conventional synthesis reactions, in order to synthesize pentafluorophenyl magnesium bromide, which is an intermediate, in the process for synthesizing bis(pentafluorophenyl)dialkyltin, which is a final object. As a result, we have reached a different synthesis route which has less side reaction and is less colored by produced impurities. Specifically, the different synthesis route is to carry out the Grignard exchange reaction, and we have invented a new synthesis route to obtain bis (pentafluorophenyl)dialkylthin, which is the final object, efficiently and with less coloring, by further reacting pentafluorophenyl magnesium bromide, which is the intermediate synthesized by the different synthesis route (the Grignard exchange reaction), with dialkyltin dichloride.

Since fluoroaryl magnesium halide, specifically, pentafluorophenyl magnesium bromide, which is the foregoing intermediate, has less side reaction in the synthesis route adopted in the present invention, the obtained pentafluorophenyl magnesium bromide is not colored. Therefore, it is possible to use the pentafluorophenyl magnesium bromide for the next process without purifying it. Besides, when the fluoroaryl magnesium halide is further reacted with an organic metal compound, even after a series of processes, specifically, even after consecutive processes, it is also possible to obtain a less colored fluoroaryl metal compound, which is the final object. Consequently, the synthesis route of the present invention is a very useful synthesis route which can simplify a series of processes. That is, in the production method of the present invention, it is possible to obtain the fluoroaryl metal compound, specifically, bis(pentafluorophenyl)dialkyltin, which is the final object, by further reacting the fluoroaryl magnesium halide, specifically, pentafluorophenyl magnesium bromide, which is the intermediate, with the organic metal compound in a series of processes, without purifying the fluoroaryl magnesium halide. More specific structure will be described below.

In order to solve the foregoing problems and to attain the foregoing object, a method for producing a fluoroaryl metal compound of the present invention, which is represented by General Formula (5):

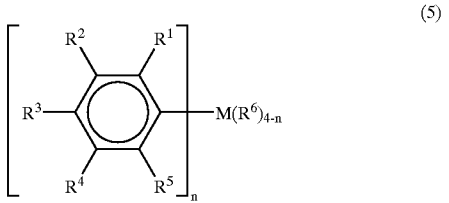

(5)

where each of $R^1$, $R^2$, $R^3$, $R^4$, and $R^5$ independently represents one of a hydrogen atom, a fluorine atom, a hydrocarbon group, and an alkoxy group, provided that at least three of $R^1$–$R^5$ represent fluorine atoms, M represents a metal atom which belongs to the group IV, $R^6$ represents a hydrocarbon group, and n represents one of 1 through 3, is characterized by including the steps of:

reacting hydrocarbon magnesium halide represented by General Formula (1):

$$R^7 MgX_a \quad (1)$$

where $R^7$ represents a hydrocarbon group, and $X_a$ represents one of a chlorine atom, a bromine atom, and an iodine atom, with fluoroaryl halide represented by General Formula (2):

(2)

where each of $R^1$, $R^2$, $R^3$, $R^4$, and $R^5$ independently represents one of a hydrogen atom, a fluorine atom, a hydrocarbon group, and an alkoxy group, provided that at least three of $R^1$–$R^5$ represent fluorine atoms, and $X_c$ represents one of a bromine atom and an iodine atom, in a solvent including an ether solvent, so as to obtain fluoroaryl magnesium halide represented by General Formula (3):

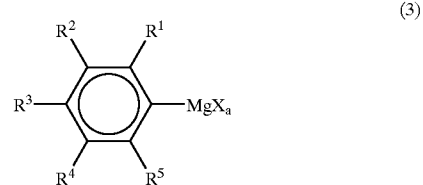

(3)

where each of $R^1$, $R^2$, $R^3$, $R^4$, and $R^5$ independently represents one of a hydrogen atom, a fluorine atom, a hydrocarbon group, and an alkoxy group, provided that at least three of $R^1$–$R^5$ represent fluorine atoms, and $X_a$ represents one of a chlorine atom, a bromine atom, and an iodine atom; and reacting the fluoroaryl magnesium halide with an organic metal compound represented by General Formula (4):

$$(R^6)_{4-n}M(X_b)_n \quad (4)$$

where $R^6$ represents a hydrocarbon group, n represents one of 1 through 3, M represents a metal atom which belongs to the group IV, and $X_b$ represents a halogen atom.

A more specific embodiment of the method for producing the fluoroaryl metal compound of the present invention is further characterized in that the metal atom in the organic metal compound represented by General Formula (4) is tin.

A more specific embodiment of the method for producing the fluoroaryl metal compound of the present invention is characterized in that the fluoroaryl metal compound, which is the object compound, is bis(pentafluorophenyl)dialkyltin.

In the present invention, since the fluoroaryl magnesium halide is first synthesized by a specific synthesis route, that is, the fluoroaryl magnesium halide is prepared beforehand by carrying out the Grignard exchange reaction, the fluoroaryl magnesium halide less colored by a by-product can be obtained. Then, by using the less colored fluoroaryl magnesium halide as an intermediate material and further reacting it with an organic metal compound, specifically, an organic tin compound, a less colored fluoroaryl metal compound can be obtained as the final object. Besides, in order to separate the fluoroaryl metal compound, which is the object, and the magnesium halide, which is the by-product, after the reaction, it is a preferable embodiment of the production method of the present invention to carry out a purifying method (a) for precipitating the magnesium halide out of the reaction solution and filtering the precipitation, or a purifying method (b) for treating the reaction solution with an acid and easily removing impurities. The specific technique in the foregoing method (a) is a technique in which a hydrocarbon solvent such as hexane, a solvent which does not dissolve the magnesium halide, is added, precipitated as solid matter and filtered. In this manner, by carrying out a process to further purify the less colored fluoroaryl metal compound, which is the object obtained as a result of the Grignard exchange reaction carried out with the organic metal compound, as one process in a series of processes, the fluoroaryl metal compound which is less colored and has no impurities can be easily and inexpensively produced, and easily and inexpensively purified.

Other objects, features, and advantages of the present invention will be fully understood by the following description. Also, benefits of the present invention will be apparent from the following explanation.

DESCRIPTION OF THE EMBODIMENTS

The following description will describe one embodiment of the present invention.

A method for producing a fluoroaryl metal compound in accordance with the present invention is a method for reacting fluoroaryl magnesium halide, obtained by reacting hydrocarbon magnesium halide with fluoroaryl halide in a solvent including an ether solvent, specifically, obtained by the Grignard exchange reaction, with an organic metal compound.

The hydrocarbon magnesium halide used as a starting material in the present invention is a compound represented by General Formula (1):

$$R^7 MgX_a \tag{1}$$

where $R^7$ represents a hydrocarbon group, and $X_a$ represents a chlorine atom, a bromine atom, or an iodine atom. Examples of the hydrocarbon group denoted as $R^7$ in the formula specifically include: an aryl group such as a phenyl group; a straight-chain, or branched-chain alkyl group having 1 through 12 carbon atoms, or cyclic alkyl group having 3 through 12 carbon atoms; and a straight-chain, or branched-chain alkenyl group having 2 through 12 carbon atoms, or cyclic alkenyl group having 3 through 12 carbon atoms. Examples of the alkyl group specifically include a methyl group, an ethyl group, a propyl group, an isopropyl group, a butyl group, an isobutyl group, a t-butyl group, a pentyl group, an isopentyl group, a t-pentyl group, a hexyl group, an octyl group, a cyclopropyl group, a cyclobutyl group, a cyclopentyl group, and a cyclohexyl group. Examples of the alkenyl group specifically include an allyl group. In the above-mentioned hydrocarbon group, the phenyl group, the ethyl group, the propyl group, the isopropyl group, the cyclohexyl group, and the allyl group are more preferable. The hydrocarbon group may further include a functional group which includes an atom inert to the reaction and purifying (treatment) in accordance with the present invention, for example, a fluorine atom, a nitrogen atom, an oxygen atom, a sulfur atom, etc., that is, an inert functional group. Examples of the functional group specifically include a methoxy group, a methylthio group, an N,N-dimethylamino group, an o-anise group, a p-anise group, a trimethylsilyloxy group, a dimethyl-t-butylsilyloxy group, and a trifluoromethyl group.

The hydrocarbon magnesium halide, which is a Grignard reagent, can be easily obtained by, for example, reacting an adequate kind of hydrocarbon halide with magnesium using a general technique. Examples of the hydrocarbon magnesium halide include hydrocarbon magnesium bromide such as ethyl magnesium bromide.

The fluoroaryl halide used as a starting material in the present invention is a compound represented by General Formula (2):

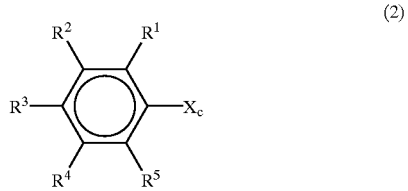

where each of $R^1$, $R^2$, $R^3$, $R^4$, and $R^5$ independently represents a hydrogen atom, a fluorine atom, a hydrocarbon group, or an alkoxy group, provided that at least three of $R^1$ through $R^5$ represent fluorine atoms, and $X_c$ represents a bromine atom or an iodine atom. Examples of the hydrocarbon group in substituents denoted as $R^1$ through $R^5$ in the formula include an aryl group such as a phenyl group; a straight-chain, or branched-chain alkyl group having 1 through 12 carbon atoms, or cyclic alkyl group having 3 through 12 carbon atoms; and a straight-chain, or branched-chain alkenyl group having 2 through 12 carbon atoms, or cyclic alkenyl group having 3 through 12 carbon atoms. Examples of the alkyl group specifically include a methyl group, an ethyl group, a propyl group, an isopropyl group, a butyl group, an isobutyl group, a t-butyl group, a pentyl group, an isopentyl group, a t-pentyl group, a hexyl group, an octyl group, a cyclopropyl group, a cyclobutyl group, a cyclopentyl group, and a cyclohexyl group. Examples of the alkenyl group specifically include an allyl group. Incidentally, the hydrocarbon group may further include a functional group including an atom inert to the reaction and purifying (treatment) in accordance with the present invention, for example, a fluorine atom, a nitrogen atom, an oxygen atom, a sulfur atom, etc., that is, an inert functional group. Examples of the functional group specifically include a methoxy group, a methyltio group, an N,N-dimethylamino group, an o-anise group, a p-anise group, a trimethylsilyloxy group, a dimethyl-t-butylsilyloxy group, and a trifluoromethyl group.

In the formula, the alkoxy group in the substituents denoted as $R^1$ through $R^5$ is represented by General Formula (A):

$$-OR_a \tag{A}$$

where $R_a$ represents a hydrocarbon group. Examples of the hydrocarbon group denoted as $R_a$ in the formula specifically include: an aryl group such as a phenyl group; a straight-chain, or branched-chain alkyl group having 1 through 12 carbon atoms, or cyclic alkyl group having 3 through 12 carbon atoms; and a straight-chain, or branched-chain alkenyl group having 2 through 12 carbon atoms, or cyclic alkenyl group having 3 through 12 carbon atoms. The hydrocarbon group may further include a functional group which includes an atom inert to the reaction and purifying (treatment) in accordance with the present invention. Examples of the alkoxy group expressed by General Formula (A) specifically include a methoxy group, an ethoxy group, an n-propoxy group, an isopropoxy group, an n-butoxy group, an isobutoxy group, a sec-butoxy group, a t-butoxy group, a cyclohexyloxy group, an allyloxy group, and a phenoxy group.

Therefore, examples of the fluoroaryl halide specifically include bromopentafluorobenzene, iodopentafluorobenzene, 1-bromo-2,3,4,5-tetrafluorobenzene, 1-bromo-2,3,4,6-tetrafluorobenzene, 1-bromo-2,3,5,6-tetrafluorobenzene, 1-iodo-2,3,4,5-tetrafluorobenzene, 1-iodo-2,3,4,6-tetrafluorobenzene, 1-iodo-2,3,5,6-tetrafluorobenzene, 1-bromo-2,3,4-trifluorobenzene, 1-bromo-2,3,5-trifluorobenzene, 1-bromo-2,4,5-trifluorobenzene, 1-bromo-2,4,6-trifluorobenzene, 1-bromo-3,4,5-trifluorobenzene, 1-iodo-2,3,4-trifluorobenzene, 1-iodo-2,3,5-trifluorobenzene, 1-iodo-2,4,5-trifluorobenzene, 1-iodo-2,4,6-trifluorobenzene, and 1-iodo-3,4,5-trifluorobenzene.

Examples of the ether solvent included in the solvent used for reacting the hydrocarbon magnesium halide with the fluoroaryl halide specifically include: chain ether solvents including dimethyl ether, diethyl ether, dipropyl ether, diisopropyl ether, dibutyl ether, diisobutyl ether, di-t-butyl ether, dipentyl ether, dihexyl ether, dioctyl ether, t-butylmethyl ether, dimethoxy methane, diethoxy methane, 1,2-dimethoxy ethane, and 1,2-diethoxy ethane; cyclic ether solvents including tetrahydrofuran, tetrahydropyran, 1,4-dioxane, and 1,3-dioxolane; and aromatic ether solvents including anisole and phenetole. One kind or a mixture of two or more kinds selected from these example ether solvents can be used effectively. Of all these example ether solvents, ether solvents including dipropyl ether, diisopropyl ether, dibutyl ether, diisobutyl ether, di-t-butyl ether, t-butylmethyl ether, 1,2-dimethoxy ethane, 1,2-diethoxy ethane, anisole, and phenetole are more preferable, in terms of convenience of the solvent, reactivity, yield, and separation of an object.

Besides, examples of other solvents which can be used together with the ether solvent specifically include aliphatic hydrocarbon solvents including pentane, hexane, heptane, and octane; alicyclic hydrocarbon solvents including cyclopentane, cyclohexane, cycloheptane, and methylcyclohexane; and aromatic hydrocarbon solvents including benzene, toluene, and xylene. The solvents can be used as long as they are the compounds which do not interfere with the reaction in accordance with the present invention. The solvents may be hydrocarbon solvents such as IsoparC, IsoparE, and IsoparG (all of them are trademarks), which are commercially available hydrocarbon solvents manufactured by Exxon Corporation. As a solvent including an ether solvent, the solvent used when forming the hydrocarbon magnesium halide by reacting hydrocarbon halide with magnesium may also be used.

Generally, when preparing fluoroaryl magnesium halide by reacting fluoroaryl halide with magnesium, which is the Grignard reaction, diethyl ether or tetrahydrofuran is usually used as a solvent, since the reaction does not proceed (the reactivity becomes low) when using a solvent such as diisopropyl ether or dibutyl ether. However, in the Grignard exchange reaction of the hydrocarbon magnesium halide and the fluoroaryl halide in the production method in accordance with the present invention, the reaction can proceed even when a solvent such as diisopropyl ether or dibutyl ether is used. Therefore, there is no need to use diethyl ether, which is a compound having a low boiling point, or tetrahydrofuran having the property of ring-opening polymerization, as a solvent. Besides, the Grignard exchange reaction can prepare less colored fluoroaryl magnesium halide, resulting in obtaining a less colored fluoroaryl metal compound.

As for the method for mixing the hydrocarbon magnesium halide with the fluoroaryl halide, various methods can be adopted, for example, a method in which a solution of the hydrocarbon magnesium halide is dropped to the fluoroaryl halide or its solution; a method in which the fluoroaryl halide or its solution is dropped to a solution of the hydrocarbon magnesium halide; and the fluoroaryl halide or its solution and a solution of the hydrocarbon magnesium halide are dropped to the solvent, etc.

As for conditions for the foregoing reaction, it is more preferable that the molar ratio between the hydrocarbon magnesium halide and the fluoroaryl halide is within the range of 0.8:1 to 2.0:1, and it is further preferable that it is within the range of 0.9:1 to 1.5:1. Within this range, less impurities are produced as by-products, and a less colored fluoroaryl magnesium halide can be obtained. It is more preferable that the amount of the solvent used for the reaction is enough to make the concentration of the obtained fluoroaryl magnesium halide within the range of 0.1 wt % to 80 wt %, further preferably, within the range of 1.0 wt % to 70 wt %. It is more preferable that the minimum value of reaction temperature is more than −30° C., further preferably, more than −20° C. It is more preferable that the maximum value of the reaction temperature is less than the reflux temperature of the solvent, and when the reflux temperature exceeds 200° C., it is further preferable that the maximum value of the reaction temperature is less than 200° C. Reaction time may be satisfactorily determined according to the combination of the hydrocarbon magnesium halide and the fluoroaryl halide, and the reaction temperature, etc. Furthermore, it is desirable that the foregoing reaction is carried out in an atmosphere of an inert gas such as a nitrogen gas. The fluoroaryl magnesium halide is obtained in the form of a reaction solution dissolved or suspended in the foregoing solvent (a solution or a suspension). Incidentally, it is possible to carry out a next reaction without removing the hydrocarbon halide ($R^7X_c$) produced with the fluoroaryl magnesium halide as a by-product from the reaction system, but it may be removed from the reaction system as necessary.

The organic metal compound used as a raw material in the present invention is a compound represented by General Formula (4):

$$(R^6)_{4-n}M(X_b)_n \tag{4}$$

where $R^6$ represents a hydrocarbon group, n represents 1 through 3, M represents a metal atom which belongs to the group IV, and $X_b$ represents a halogen atom. Examples of the hydrocarbon group denoted as $R^6$ in the formula specifically include substituents as in the case of the hydrocarbon group denoted as $R^7$. Of the substituents, a methyl group, an ethyl group, a propyl group, an isopropyl group, a butyl group, an isobutyl group, and a t-butyl group are more preferable. Tin is particularly preferable as a metal atom which belongs to the group IV (in short periodic type: the groups 4 and 14 in long periodic type) denoted as M in the formula. It is more preferable that $X_b$ in the organic metal compound is a chlorine atom or a bromine atom. Further, it is more preferable that n in the formula is 2. Examples of the organic metal compound include organic metal chlorides including dimethyltin dichloride, diethyltin dichloride, dibutyltin dichloride, dimethyltin dibromide, diethyltin dibromide, and dibutyltin dibromide.

By reacting the fluoroaryl magnesium halide obtained by the foregoing method with the organic metal compound in the solvent, a fluoroaryl metal compound represented by General Formula (5):

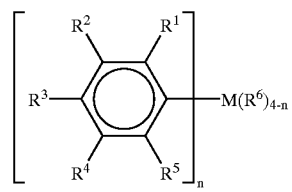

(5)

where each of $R^1$, $R^2$, $R^3$, $R^4$, and $R^5$ independently represents a hydrogen atom, a fluorine atom, a hydrocarbon group, or an alkoxy group, provided that at least three of $R^1$ through $R^5$ represent fluorine atoms, M represents a metal atom which belongs to the group IV, $R^6$ represents a hydrocarbon group, and n represents 1 through 3, is obtained.

As for the method for mixing the fluoroaryl magnesium halide and the organic metal compound, various methods can be adopted, such as a method in which the organic metal compound is added to a solution of the fluoroaryl magnesium halide, that is, the reaction solution obtained in the foregoing reaction; and a method in which the reaction solution obtained in the foregoing reaction is added to the organic metal compound. Incidentally, the organic metal compound may be in the form of a solution diluted by the solvent or a suspended suspension.

As for conditions for the foregoing reaction, it is more preferable that the molar ratio between the fluoroaryl magnesium halide and the organic metal compound is within the range of 0.1:1 to 10:1, and it is further preferable that it is within the range of 0.5:1 to 5:1. It is more preferable that the amount of the solvent used for the reaction is enough to make the concentration of the fluoroaryl metal compound, which is the object, within the range of 0.1 wt % to 80 wt %, further preferably, within the range of 1.0 wt % to 70 wt %. It is more preferable that the minimum value of reaction temperature is more than −30° C., further preferably, more than −20° C. It is more preferable that the maximum value of the reaction temperature is less than the reflux temperature of the solvent, and when the reflux temperature exceeds 200° C., it is further preferable that the maximum value of the reaction temperature is less than 200° C. Reaction time may be satisfactorily determined according to the combination of the fluoroaryl magnesium halide and the organic metal compound, and the reaction temperature, etc. The fluoroaryl metal compound is obtained in the form of a reaction solution dissolved in the foregoing solvent. Incidentally, it is desirable that the foregoing reaction is carried out in an atmosphere of an inert gas such as a nitrogen gas.

The fluoroaryl metal compound obtained by the foregoing method is a metal compound having at least one fluoroaryl group in which at least three hydrogen atoms in the aryl group are substituted by fluorine atoms. As the fluoroaryl group, a pentafluorophenyl group is more preferable. Besides, it is more preferable that n in the foregoing formula is 2. Therefore, as the fluoroaryl metal compound, bis(pentafluorophenyl)dialkyltin such as bis(pentafluorophenyl)dimethyltin, bis(pentafluorophenyl)dibutyltin, etc. is particularly preferable.

In the foregoing method, along with the fluoroaryl metal compound, which is the object, magnesium halide which is represented by General Formula (6):

$$MgX_aX_b \qquad (6)$$

where $X_a$ represents a chlorine atom, a bromine atom, or an iodine atom, and $X_b$ represents a halogen atom, is also obtained as a by-product, in the form of a solution containing the fluoroaryl metal compound, the magnesium halide, and the ether solvent, or in the form of a suspension in which the magnesium halide is precipitated.

Specifically, the magnesium halide is at least one component selected from the group consisting of magnesium fluoride chloride, magnesium fluoride bromide, magnesium fluoride iodide, magnesium dichloride, magnesium chloride bromide, magnesium chloride iodide, magnesium dibromide, magnesium bromide iodide, and magnesium diiodide. The production method of the present invention can be applied also to a reaction system in which these compounds are mixed.

As the ether solvent contained in the solution containing the fluoroaryl metal compound and the magnesium halide, ether contained in the solvent used when reacting the hydrocarbon magnesium halide with the fluoroaryl halide can be specifically named, so the explanation will be omitted here.

In order to remove the magnesium halide from the foregoing solution or suspension, when the magnesium halide is obtained as the solution, it is preferable to (A) precipitate and deposit the magnesium halide and remove it, or (B) purify the solution by treating it with an acid. When the magnesium halide is obtained as the suspension, it is preferable to (C) filter the suspension, or (B) purify the suspension by treating it with an acid. One type or a mixture of two or more types selected from these processing methods can be used effectively.

Examples of the method (A) for precipitating and depositing the magnesium halide as solid matter specifically include: (1) a method in which the foregoing solution is mixed with a solvent which does not dissolve the magnesium halide (hereinafter referred to as a solvent A); (2) a method in which a residue (a concentrated solution) obtained by distilling out the ether solvent from the foregoing solution and the solvent A are mixed; (3) a method in which the foregoing solution is mixed with a solvent which has a boiling point higher than that of the ether solvent contained in the foregoing solution and which does not dissolve the magnesium halide (hereinafter referred to as a solvent B), then the ether solvent is distilled out from the mixed solution, and the concentrated solution is cooled as necessary; (4) a method in which the solvent B is heated to a temperature higher than the boiling point of the ether solvent contained in the foregoing solution, then the ether solvent is distilled out with the foregoing solution being added to the solvent B, and the concentrated solution is cooled as necessary, etc.

Examples of the solvents A and B specifically include: aliphatic hydrocarbon solvents such as pentane, hexane, heptane, and octane, etc.; alicyclic hydrocarbon solvents such as cyclopentane, cyclohexane, cycloheptane, and methylcyclohexane; aromatic hydrocarbon solvents such as benzene, toluene, and xylene; and ether solvents such as diisopropyl ether, and dibutyl ether. One kind or a mixture of two or more kinds selected from these example solvents can be used as the solvent A or B. The amount of the solvent A or B used with respect to the solution is satisfactorily specified as long as they are sufficient to carry out purifying effectively. When two or more kinds of the solvents are used so as to constitute the solvent A or B, the proportions of the respective solvents in the solvent A or B can be specified conveniently. Besides, as the solvent A or B, mixed hydrocarbon solvents such as IsoparC, IsoparE, and IsoparG, which are commercially available hydrocarbon solvents, may also be used.

As for the method for mixing the solution and the solvent A in the foregoing methods (1) and (2), the solvent A may be added to the solution, or the solution may be added to the solvent A. Specifically, the temperature when mixing the solution and the solvent A is, more preferably, within the range of −100° C. to 200° C., further preferably, within the range of −50° C. to 150° C., and most preferably, within the range of −20° C. to 120° C.

As for the method for mixing the solution and the solvent B in the foregoing method (3), the solvent B may be added to the solution, or the solution may be added to the solvent B. Specifically, the temperature when mixing the solution and the solvent B is, more preferably, within the range of −100° C. to 200° C., further preferably, within the range of −50° C. to 150° C.

As for the method for distilling out the ether solvent in the foregoing methods (2) to (4), specifically, a method for heating the solution or the mixed solution under a normal pressure (atmospheric pressure) can be adopted. However, a method for heating the solution or the mixed solution under a reduced or increased pressure may also be adopted. When the ether solvent is distilled out under a normal pressure, the heating temperature is satisfactorily specified as long as it is more than the boiling point of the ether solvent. Further, the cooling temperature when cooling the concentrated solution obtained by distilling out the ether solvent in the foregoing methods (3) and (4) is satisfactorily specified so that the magnesium halide is sufficiently precipitated.

The magnesium halide can be precipitated and deposited as solid matter by carrying out the foregoing methods (1) to (4), etc. The magnesium halide can be separated and removed by filtering the solution (concentrated solution) containing the fluoroaryl metal compound and the solvent A or B. In this manner, the fluoroaryl metal compound can be purified easily and inexpensively. Consequently, the fluoroaryl metal compound can be produced easily and inexpensively. That is, a highly-pure fluoroaryl metal compound without having impurities can be obtained easily and inexpensively.

Examples of the method for treating the solution with an acid specifically include: (5) a method in which the foregoing solution or suspension and an aqueous solution containing an acid are mixed and stirred, then the mixed solution is allowed to stand so as to be separated into an organic layer containing the fluoroaryl metal compound and an aqueous layer containing the magnesium halide and the acid, and the aqueous layer is removed. The magnesium halide is dissolved in the aqueous solution containing the acid, but the fluoroaryl metal compound is insoluble into the aqueous solution.

As the foregoing acid, inorganic acids and/or organic acids can be used. Examples of the acid specifically include: inorganic acids such as hydrochloric acid, sulfuric acid, nitric acid, phosphoric acid, and carbonic acid, etc.; and organic acids such as formic acid, acetic acid, propionic acid, oxalic acid, malonic acid, and succinic acid, etc. One kind or a mixture of two or more kinds, such as a mixture of an inorganic acid and an organic acid, selected from these example acids can be used. As for the acid which can be used in the present invention, at least one kind of acid selected from the group consisting of hydrochloric acid, sulfuric acid, nitric acid, phosphoric acid, carbonic acid, formic acid, acetic acid, propionic acid, oxalic acid, malonic acid, and succinic acid is preferable. Of these example acids, at least one type of acid selected from the group consisting of hydrochloric acid, sulfuric acid, nitric acid, phosphoric acid, formic acid, acetic acid, oxalic acid, malonic acid, and succinic acid is more preferable. It is preferable that the amount of the acid to be used is more than 0.01 equivalent, more preferably, more than 0.1 equivalent, with respect to the magnesium halide contained in the solution, so as to efficiently carry out purifying. The concentration of the acid in the aqueous solution and the method for preparing the aqueous solution containing the acid can be specified conveniently. When two or more kinds of the acids are used, the proportions of the respective acids can be specified conveniently.

As for the method for mixing the solution with the aqueous solution containing the acid in the foregoing method (5), the aqueous solution may be added to the solution, or the solution may be added to the aqueous solution. It is preferable that the temperature when mixing and stirring the solution and the aqueous solution containing the acid is higher than the temperature at which the fluoroaryl metal compound is precipitated out of the solution, and less than the temperature at which the fluoroaryl metal compound is decomposed. Specifically, the range of −100° C. to 200° C. is preferable, the range of −50° C. to 150° C. is more preferable, and the range of −20° C. to 100° C. is further preferable. The period of time when mixing the solution and the aqueous solution containing the acid can be specified conveniently.

The organic layer and the aqueous layer can be separated by a simple procedure such as liquid separating (oil water separating) procedure, but the method for separating the organic layer and the aqueous layer and the method for removing the aqueous layer, that is, the method for removing the magnesium halide and the acid, is not limited to the foregoing method (5). When the acid is contained in the organic layer, it is satisfactory to carry out a simple procedure, for example, washing the organic layer with water, an aqueous solution of sodium carbonate, an aqueous solution of sodium hydrogen carbonate, or an aqueous solution of sodium hydroxide, etc., as necessary. When the fluoroaryl metal compound is contained in the aqueous layer, it is satisfactory to carry out a simple procedure, for example, extracting (recovery) the fluoroaryl metal compound from the aqueous layer using an appropriate solvent, as necessary. Further, when water is contained in the organic layer, it is satisfactory to remove (dry) the water by adding a desiccating agent such as magnesium sulfate, anhydrous to the organic layer, as necessary. Incidentally, the method for treating the solution with the acid, such as the foregoing method (5), may be carried out repeatedly as necessary, so that the magnesium halide contained in the solution is sufficiently removed.

By carrying out the foregoing method (5) or the like, the magnesium halide can be separated and removed. Thus, the fluoroaryl metal compound can be produced easily and inexpensively. That is, a highly pure fluoroaryl metal compound having no impurities can be obtained easily and inexpensively.

In the following, the present invention will be explained in detail by way of examples and a comparative example, but the present invention is not limited to the disclosure below. Incidentally, the NMR (Nuclear Magnetic Resonance) spectrum data in the examples were measured, using tetramethylsilane (TMS) as a reference material in the case of $^1$H-NMR spectrum data, and using trifluoroacetic acid as a reference material in the case of $^{19}$F-NMR spectrum data. The signal of the reference material was set at 0 ppm.

EXAMPLE 1

The following description will show a reaction process by way of fluoroaryl magnesium halide obtained by the Grignard exchange reaction.

First, 3.23 g (0.133 mol) of magnesium was charged to a reaction vessel equipped with a reflux condenser, a thermometer, a dropping funnel, a nitrogen gas conduit, and a stirrer, and air inside the reaction vessel was satisfactorily displaced by a nitrogen gas. Next, 150 ml of diisopropyl ether as a solvent was charged to the reaction vessel, and 13.43 g (0.123 mol) of ethyl bromide was charged to the dropping funnel. Then, the ethyl bromide was dropped from the dropping funnel over two hours, with stirring the content of the reaction vessel at room temperature under a nitrogen gas atmosphere. When the dropping was completed, the content was further stirred at room temperature for 30 minutes and maturated. On the other hand, 29.99 g (0.121 mol) of bromopentafluorobenzene as fluoroaryl halide was charged to the dropping funnel.

Next, the bromopentafluorobenzene was dropped from the dropping funnel over two hours, with stirring the content of the reaction vessel at room temperature under the nitrogen gas atmosphere. When the dropping was completed, the content was further stirred at room temperature for 30 minutes and maturated. Consequently, pentafluorophenyl magnesium bromide was obtained as an isopropyl ether suspension. This reaction solution was not colored. When the maturation was completed, 17.54 g (0.058 mol) of dibutyltin dichloride as an organic metal compound was charged to the reaction vessel, without isolating the pentafluorophenyl magnesium bromide, and the content was stirred at room temperature for three hours.

When the reaction was completed, precipitated deposits (magnesium chloride bromide) were filtered off. Next, 100 ml of hexane was added to the residue obtained by concentrating the filtrate so as to precipitate impurities contained in the residue, then the imputiries were removed by being filtered. Then, the filtrate was concentrated so as to obtain 31.24 g of bis(pentafluorophenyl)dibutyltin as a fluoroaryl metal compound, obtained as a colorless liquid.

As a result of analysis by a $^{19}$F-NMR, the yield of the bis(pentafluorophenyl)dibutyltin was 95.4% based on dibutyltin dichloride, and the purity was 99.2%. The NMR spectrum data of the obtained bis(pentafluorophenyl)dibutyltin was as follows:

$^1$H-NMR(benzene-d$_6$, δ) 0.84(6H, t, J=7.2 Hz), 1.26(4H, m), 1.50(8H, m); $^{19}$F-NMR(benzene-d$_6$, δ): −45.7, −74.4, −83.6.

EXAMPLE 2

The following description will show a reaction process by way of fluoroaryl magnesium halide obtained by the Grignard exchange reaction.

First, 10.00 g (0.411 mol) of magnesium was charged to a first reaction vessel similar to the reaction vessel in Example 1, and air inside the first reaction vessel was satisfactorily displaced by a nitrogen gas. Next, 300 ml of dibutyl ether as a solvent was charged to the first reaction vessel, and 39.70 g (0.364 mol) of ethyl bromide was charged to a dropping funnel. Then, the ethyl bromide was dropped from the dropping funnel over two hours, with stirring the content of the first reaction vessel and keeping the inside temperature at 30° C. to 40° C. under a nitrogen gas atmosphere. When the dropping was completed, the content was further stirred at the same temperature for 30 minutes and maturated. On the other hand, 90.00 g (0.364 mol) of bromopentafluorobenzene was charged to the dropping funnel.

Next, the bromopentafluorobenzene was dropped from the dropping funnel over two hours, with stirring the content of the first reaction vessel and keeping the inside temperature at 30° C. to 40° C. under the nitrogen gas atmosphere. When the dropping was completed, the content was further stirred at the same temperature for one hour and maturated. Consequently, a dibutyl ether solution of pentafluorophenyl magnesium bromide was obtained. As in Example 1, the solution was not colored.

Then, 38.60 g (0.176 mol) of dimethyltin dichloride as an organic metal compound was charged to a second reaction vessel similar to the reaction vessel in Example 1, and air inside the second reaction vessel was satisfactorily displaced by a nitrogen gas. Next, 100 ml of dibutyl ether was charged to the second reaction vessel, and the dibutyl ether solution of the pentafluorophenyl magnesium bromide was charged to a dropping funnel. Then, the dibutyl ether solution was dropped from the dropping funnel over two hours, with stirring the content of the second reaction vessel and keeping the inside temperature at 30° C. to 40° C. under a nitrogen gas atmosphere. When the dropping was completed, the content was further stirred at the same temperature for one hour.

When the reaction was completed, precipitated deposits (magnesium chloride bromide) were filtered off, then bis(pentafluorophenyl)dimethyltin as a fluoroaryl metal compound was obtained as a colorless dibutyl ether solution. The reaction yield was analyzed by a $^{19}$F-NMR. That is, $^{19}$F-NMR was measured under predetermined conditions, using p-fluorotoluene as an internal reference. Then, an integral value of a fluorine atom of the p-fluorotoluene and an integral value of a fluorine atom of an ortho position of a pentafluorophenyl group of the bis(pentafluorophenyl)dimethyltin were given from the obtained $^{19}$F-NMR chart, and the amount of the bis(pentafluorophenyl)dimethyltin was calculated from these two integral values. As a result, the yield of the bis(pentafluorophenyl)dimetyltin was 97.5% based on dimethyltin dichloride, and the purity was 99.0%.

EXAMPLE 3

The following description will show a reaction process by way of fluoroaryl magnesium halide obtained by the Grignard exchange reaction.

First, 5.00 g (0.206 mol) of magnesium was charged to a first reaction vessel similar to the reaction vessel in Example 1, and air inside the first reaction vessel was satisfactorily displaced by a nitrogen gas. Next, 150 ml of dibutyl ether was charged to the first reaction vessel, and 19.81 g (0.182 mol) of ethyl bromide was charged to a dropping funnel. Then, the ethyl bromide was dropped from the dropping funnel over two hours, with stirring the content of the first reaction vessel and keeping the inside temperature at 30° C. to 40° C. under a nitrogen gas atmosphere. When the dropping was completed, the content was further stirred at the same temperature for 30 minutes and maturated. On the other hand, 45.00 g (0.182 mol) of bromopentafluorobenzene was charged to the dropping funnel.

Next, the bromopentafluorobenzene was dropped from the dropping funnel over two hours, with stirring the content of the first reaction vessel and keeping the inside temperature at 30° C. to 40° C. under the nitrogen gas atmosphere. When the dropping was completed, the content was further stirred at the same temperature for one hour and maturated. Consequently, a dibutyl ether solution of pentafluorophenyl magnesium bromide was obtained. As in Examples 1 and 2, the solution was not colored.

Then, 19.30 g (0.088 mol) of dimethyltin dichloride was charged to a second reaction vessel similar to the reaction vessel in Example 1, and air inside the second reaction vessel was satisfactorily displaced by a nitrogen gas. Next, 100 ml of hexane as a solvent was charged to the second reaction vessel, and the dibutyl ether solution of the pentafluorophenyl magnesium bromide was charged to a dropping funnel. Then, the dibutyl ether solution was dropped from the dropping funnel over two hours, with stirring the content of the second reaction vessel and keeping the inside temperature at 30° C. to 40° C. under a nitrogen gas atmosphere. When the dropping was completed, the content was further stirred at the same temperature for one hour.

When the reaction was completed, precipitated deposits (magnesium chloride bromide) were filtered off. Next, 100 ml of hexane was added to the residue obtained by distilling out the solvent in the filtrate under a reduced pressure so as to precipitate impurities contained in the residue, then the imputiries were removed by filtration. Then, the filtrate was concentrated so as to obtain 39.5 g of bis(pentafluorophenyl)dimethyltin as a colorless liquid. As a result of analysis by a $^{19}$F-NMR, the yield of the bis(pentafluorophenyl)dimethyltin was 93.0% based on dimethyltin dichloride, and the purity was 98.5%.

EXAMPLE 4

The following description will show a reaction process by way of fluoroaryl magnesium halide obtained by the Grignard exchange reaction.

First, 5.00 g (0.206 mol) of magnesium was charged to a first reaction vessel similar to the reaction vessel in Example 1, and air inside the first reaction vessel was satisfactorily displaced by a nitrogen gas. Next, 88 g of t-butylmethyl ether was charged to the first reaction vessel, and 21.47 g (0.197 mol) of ethyl bromide was charged to a dropping funnel. Then, the ethyl bromide was dropped from the dropping funnel over 30 minutes, with stirring the content of the first reaction vessel and keeping the inside temperature at 30° C. to 40° C. under a nitrogen gas atmosphere. When the dropping was completed, the content was further stirred at the same temperature for two hours and maturated. On the other hand, 45.00 g (0.182 mol) of bromopentafluorobenzene was charged to the dropping funnel.

Next, the bromopentafluorobenzene was dropped from the dropping funnel over 30 minutes, with stirring the content of the first reaction vessel and keeping the inside temperature at 30° C. to 40° C. under the nitrogen gas atmosphere. When the dropping was completed, the content was further stirred at the same temperature for two hours and maturated. Consequently, pentafluorophenyl magnesium bromide was obtained as a t-butylmethyl ether suspension. The reaction solution was not colored.

Then, 80 g of t-butylmethyl ether was added to the reaction vessel, 19.30 g (0.088 mol) of dimethyltin dichloride as an organic metal compound was charged, and the content was stirred at room temperature for three hours.

When the reaction was completed, by filtering off the precipitates (magnesium chloride bromide), bis(pentafluorophenyl)dimethyltin as a fluoroaryl metal compound was obtained as a t-butylmethyl ether solution. As a result of analysis by a method identical to that used in Example 2, the yield of the bis(pentafluorophenyl)dimethyltin was 96.3% based on dimethyltin dichloride, and the purity was 99.0%.

EXAMPLE 5

The following description will show a reaction process by way of fluoroaryl magnesium halide obtained by the Grignard exchange reaction.

First, 4.78 g (0.197 mol) of magnesium was charged to a first reaction vessel similar to the reaction vessel in Example 1, and air inside the first reaction vessel was satisfactorily displaced by a nitrogen gas. Next, 70 g of diethyl ether was charged to the first reaction vessel, and 21.47 g (0.197 mol) of ethyl bromide was charged to a dropping funnel. Then, the ethyl bromide was dropped from the dropping funnel over 30 minutes, with stirring the content of the first reaction vessel and keeping the inside temperature at a reflux temperature of diethyl ether under a nitrogen gas atmosphere. When the dropping was completed, the content was further stirred at the same temperature for two hours and maturated. On the other hand, 45.00 g (0.182 mol) of bromopentafluorobenzene was charged to the dropping funnel.

Next, the bromopentafluorobenzene was dropped from the dropping funnel over 30 minutes, with stirring the content of the first reaction vessel and keeping the inside temperature at a reflux temperature of diethyl ether under the nitrogen gas atmosphere. When the dropping was completed, the content was further stirred at the same temperature for two hours and maturated. Consequently, a diethyl ether solution of pentafluorophenyl magnesium bromide was obtained. The reaction solution was not colored.

Then, 19.24 g (0.088 mol) of dimethyltin dichloride serving as an organic metal compound was charged to a second reaction vessel similar to the reaction vessel in Example 1, and air inside the second reaction vessel was satisfactorily displaced by a nitrogen gas. Next, 70 g of diethyl ether was charged to the second reaction vessel, and the diethyl ether solution of the pentafluorophenyl magnesium bromide was charged to a dropping funnel. Then, the diethyl ether solution was dropped from the dropping funnel over two hours, with stirring the content of the second reaction vessel and keeping the inside temperature at a reflux temperature of diethyl ether under a nitrogen gas atmosphere. When the dropping was completed, the content was further stirred at the same temperature for one hour. Consequently, the bis(pentafluorophenyl)dimethyltin as a fluoroaryl metal compound was obtained as a colorless diethyl ether solution containing magnesium chloride bromide in a dissolved state. As a result of analysis by a method identical to that used in Example 2, the yield of the bis(pentafluorophenyl)dimethyltin was 92.8% based on dimethyltin dichloride, and the purity was 98.4%.

EXAMPLE 6

The following description will show a reaction process by way of fluoroaryl magnesium halide obtained by the Grignard exchange reaction.

First, 4.78 g (0.197 mol) of magnesium was charged to a first reaction vessel similar to the reaction vessel in Example 1, and air inside the first reaction vessel was satisfactorily displaced by a nitrogen gas. Next, 70 g of diethyl ether was charged to the first reaction vessel, and 24.23 g (0.197 mol) of n-propyl bromide was charged to a dropping funnel. Then, the n-propyl bromide was dropped from the dropping funnel over 30 minutes, with stirring the content of the first reaction vessel and keeping the inside temperature at a reflux temperature of diethyl ether under a nitrogen gas atmosphere. When the dropping was completed, the content was further stirred at the same temperature for two hours and maturated. On the other hand, 45.00 g (0.182 mol) of bromopentafluorobenzene was charged to the dropping funnel.

Next, the bromopentafluorobenzene was dropped from the dropping funnel over 30 minutes, with stirring the content of the first reaction vessel and keeping the inside temperature at a reflux temperature of diethyl ether under the nitrogen gas atmosphere. When the dropping was completed, the content was further stirred at the same temperature for two hours and maturated. Consequently, a diethyl ether solution of pentafluorophenyl magnesium bromide was obtained.

Then, 19.26 g (0.088 mol) of dimethyltin dichloride as an organic metal compound was charged to a second reaction vessel similar to the reaction vessel in Example 1, and air inside the second reaction vessel was satisfactorily displaced by a nitrogen gas. Next, 70 g of diethyl ether was charged to the second reaction vessel, and the diethyl ether solution of the pentafluorophenyl magnesium bromide was charged to a dropping funnel. Then, the diethyl ether solution was dropped from the dropping funnel over two hours, with stirring the content of the second reaction vessel and keeping the inside temperature at a reflux temperature of diethyl ether under a nitrogen gas atmosphere. When the dropping was completed, the content was further stirred at the same temperature for one hour. Consequently, the bis(pentafluorophenyl)dimethyltin as a fluoroaryl metal compound was obtained as a colorless diethyl ether solution containing magnesium chloride bromide in a dissolved state. As a result of analysis by a method identical to that used in Example 2, the yield of the bis(pentafluorophenyl)

dimethyltin was 93.2% based on dimethyltin dichloride, and the purity was 98.6%.

EXAMPLE 7

The following description will show a reaction process by way of fluoroaryl magnesium halide obtained by the Grignard exchange reaction.

First, 5.00 g (0.206 mol) of magnesium was charged to a first reaction vessel similar to the reaction vessel in Example 1, and air inside the first reaction vessel was satisfactorily displaced by a nitrogen gas. Next, 150 ml of dibutyl ether was charged to the first reaction vessel, and 21.22 g (0.195 mol) of ethyl bromide was charged to a dropping funnel. Then, the ethyl bromide was dropped from the dropping funnel over 30 minutes, with stirring the content of the first reaction vessel and keeping the inside temperature at 30° C. to 40° C. under a nitrogen gas atmosphere. When the dropping was completed, the content was further stirred at the same temperature for two hours and maturated. On the other hand, 45.00 g (0.182 mol) of bromopentafluorobenzene was charged to the dropping funnel.

Next, the bromopentafluorobenzene was dropped from the dropping funnel over 30 minutes, with stirring the content of the first reaction vessel and keeping the inside temperature at 30° C. to 40° C. under the nitrogen gas atmosphere. When the dropping was completed, the content was further stirred at the same temperature for two hours and maturated. Consequently, a dibutyl ether solution of pentafluorophenyl magnesium bromide was obtained. The reaction was not colored.

Then, 19.12 g (0.087 mol) of dimethyltin dichloride was charged to a second reaction vessel similar to the reaction vessel in Example 1, and air inside the second reaction vessel was satisfactorily displaced by a nitrogen gas. Next, 100 ml of dibutyl ether was charged to the second reaction vessel, and the dibutyl ether solution of the pentafluorophenyl magnesium bromide was charged to a dropping funnel. Then, the dibutyl ether solution was dropped from the dropping funnel over two hours, with stirring the content of the second reaction vessel and keeping the inside temperature at 30° C. to 40° C. under a nitrogen gas atmosphere. When the dropping was completed, the content was further stirred at the same temperature for one hour.

Next, 250 g of an aqueous solution of 1M-hydrochloric acid as an aqueous solution containing an acid was charged to the dropping funnel. Then, the aqueous solution was dropped from the dropping funnel over one hour, with stirring the content of the second reaction vessel and keeping the temperature of the aqueous solution in the dropping funnel at not more than 40° C. When the dropping was completed, the content of the second reaction vessel was moved into a separating funnel, and allowed to stand so as to be separated into an organic layer and an aqueous layer, and the aqueous layer was drained. Consequently, the bis (pentafluorophenyl)dimethyltin as a fluoroaryl metal compound was obtained as a dibutyl ether solution. As a result of analysis by a method identical to that used in Example 2, the yield of the bis(pentafluorophenyl)dimethyltin was 95.3% based on dimethyltin dichloride, and the purity was 98.8%.

COMPARATIVE EXAMPLE 1

The following description will show an example of synthesizing pentafluorophenyl magnesium bromide by way of the conventional Grignard reagent, and an example of synthesizing bis (pentafluorophenyl)dimethyltin using the pentafluorophenyl magnesium bromide as a raw material.

First, 9.73 g (0.400 mol) of magnesium was charged to a first reaction vessel similar to that in Example 1, and air inside the first reaction vessel was satisfactorily displaced by a nitrogen gas. Next, 300 ml of diethyl ether serving as a solvent was charged to the first reaction vessel, and 90.00 g (0.364 mol) of bromopentafluorobenzene as fluoroaryl halide was charged to the dropping funnel. Then, the bromopentafluorobenzene was dropped from the dropping funnel over two hours, with stirring the content of the first reaction vessel and keeping the inside temperature at the reflux temperature of diethyl ether (35° C.) under a nitrogen gas atmosphere. When the dropping was completed, the content was further stirred at the same temperature for three hours and maturated. Consequently, a diethyl ether solution of pentafluorophenyl magnesium bromide was obtained. This reaction solution seemed to have side reaction, and was colored in black.

Then, 38.60 g (0.176 mol) of dimethyltin dichloride was charged to a second reaction vessel similar to that in Example 1, and air inside the second reaction vessel was satisfactorily displaced by a nitrogen gas. Next, 100 ml of diethyl ether was charged to the second reaction vessel, and the diethyl ether solution of the pentafluorophenyl magnesium bromide was charged to the dropping funnel. Then, the diethyl ether solution was dropped from the dropping funnel over two hours, with stirring the content of the second reaction vessel and keeping the inside temperature at the reflux temperature of diethyl ether under a nitrogen gas atmosphere. When the dropping was completed, the content was further stirred at the same temperature for one hour.

Consequently, bis(pentafluorophenyl)dimethyltin was obtained as a diethyl ether solution containing magnesium chloride bromide in a dissolved state. However, the diethyl ether solution was colored in black by impurities produced as by-products. As a result of analysis by a $^{19}$F-NMR, the yield of the bis(pentafluorophenyl)dimethyltin was 87.9% based on dimethyltin dichloride.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing a fluoroaryl metal compound represented by General Formula (5):

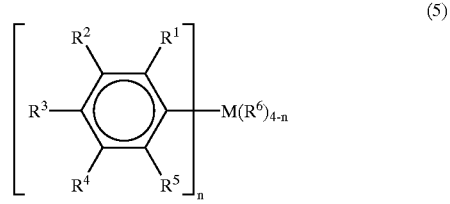

(5)

where each of $R^1$, $R^2$, $R^3$, $R^4$, and $R^5$ independently represents one of a hydrogen atom, a fluorine atom, a hydrocarbon group, and an alkoxy group, provided that at least three of $R^1$–$R^5$ represent fluorine atoms, M represents a metal atom which belongs to the group IV, $R^6$ represents a hydrocarbon group, and n represents one of 1 through 3, comprising the steps of:

reacting hydrocarbon magnesium halide represented by General Formula (1):

$$R^7MgX_a \qquad (1)$$

where $R^7$ represents a hydrocarbon group, and $X_a$ represents one of a chlorine atom, a bromine atom, and an iodine atom, with fluoroaryl halide represented by General Formula (2):

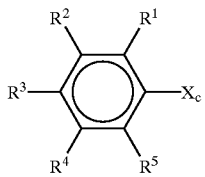
(2)

where each of $R^1$, $R^2$, $R^3$, $R^4$, and $R^5$ independently represents one of a hydrogen atom, a fluorine atom, a hydrocarbon group, and an alkoxy group, provided that at least three of $R^1$–$R^5$ represent fluorine atoms, and $X_c$ represents one of a bromine atom and an iodine atom, in a solvent including an ether solvent, so as to obtain fluoroaryl magnesium halide represented by General Formula (3):

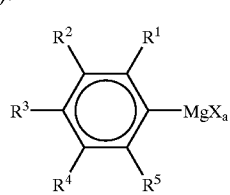
(3)

where each of $R^1$, $R^2$, $R^3$, $R^4$, and $R^5$ independently represents one of a hydrogen atom, a fluorine atom, a hydrocarbon group, and an alkoxy group, provided that at least three of $R^1$–$R^5$ represent fluorine atoms, and $X_a$ represents one of a chlorine atom, a bromine atom, and an iodine atom; and reacting said fluoroaryl magnesium halide with an organic metal compound represented by General Formula (4):

(4)

$(R^6)_{4-n}M(X_b)$ where $R^6$ represents a hydrocarbon group, n represents one of 1 through 3, M represents a metal atom which belongs to the group IV, and $X_b$ represents a halogen atom.

2. The method for producing a fluoroaryl metal compound of claim 1, wherein:

said metal atom included in said organic metal compound is tin.

3. The method for producing a fluoroaryl metal compound of claim 1, wherein:

said fluoroaryl metal compound is bis(pentafluorophenyl) dialkyltin.

4. The method for producing a fluoroaryl metal compound of claim 1, wherein:

said fluoroaryl magnesium halide is obtained in at least one ether solvent selected from the group consisting of dipropyl ether, diisopropyl ether, dibutyl ether, diisobutyl ether, di-t-butyl ether, t-butylmethyl ether, 1,2-dimethoxy ethane, 1,2-diethoxy ethane, anisole, and phenetole.

5. The method for producing a fluoroaryl metal compound of claim 1, wherein:

a molar ratio between said hydrocarbon magnesium halide and said fluoroaryl halide is within a range of 0.8:1 to 2.0:1.

6. The method for producing a fluoroaryl metal compound of claim 1, wherein:

a molar ratio between said fluoroaryl magnesium halide represented by General Formula (3) and said organic metal compound represented by General Formula (4) is within a range of 0.5:1 to 5:1.

7. The method for producing a fluoroaryl metal compound of claim 1, wherein:

a temperature when reacting said fluoroaryl magnesium halide represented by General Formula (3) with said organic metal compound represented by General Formula (4) is more than −30° C.; and its maximum value is less than a reflux temperature of said solvent.

8. The method for producing a fluoroaryl metal compound of claim 1, wherein:

said organic metal compound is at least one compound selected from the group consisting of dimethyltin dichloride, diethyltin dichloride, dibutyltin dichloride, dimethyltin dibromide, diethyltin dibromide, and dibutyltin dibromide.

9. The method for producing a fluoroaryl metal compound of claim 1, wherein:

said fluoroaryl metal compound and magnesium halide, a by-product, represented by General Formula (6):

$MgX_aX_b$ (6)

where $X_a$ represents one of a chlorine atom, a bromine atom, and an iodine atom, and $X_b$ represents a halogen atom, are obtained as a solution containing said ether solvent, and said magnesium halide is precipitated and removed from said solution.

10. The method for producing a fluoroaryl metal compound of claim 9, wherein:

said magnesium halide is precipitated and removed by adding one solvent selected from the group consisting of an aliphatic hydrocarbon solvent, an alicyclic hydrocarbon solvent, and an aromatic hydrocarbon solvent, to said ether solvent.

11. The method for producing a fluoroaryl metal compound of claim 1, wherein:

said fluoroaryl metal compound and magnesium halide, a by-product, represented by General Formula (6):

$MgX_aX_b$ (6)

where $X_a$ represents one of a chlorine atom, a bromine atom, and an iodine atom, and $X_b$ represents a halogen atom, are obtained as a solution containing said ether solvent, and said solution is treated with an acid.

12. The method for producing a fluoroaryl metal compound of claim 11, wherein:

said acid is an organic acid and/or an inorganic acid.

13. The method for producing a fluoroaryl metal compound of claim 11, wherein:

said acid is at least one acid selected from the group consisting of hydrochloric acid, sulfuric acid, nitric acid, phosphoric acid, carbonic acid, formic acid, acetic acid, propionic acid, oxalic acid, malonic acid, and succinic acid.

* * * * *